US007645460B2

(12) United States Patent
Dansereau et al.

(10) Patent No.: US 7,645,460 B2
(45) Date of Patent: *Jan. 12, 2010

(54) DOSAGE FORMS OF RISEDRONATE

(75) Inventors: Richard John Dansereau, Cincinnati, OH (US); David Ernest Burgio, Jr., Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 613 days.

This patent is subject to a terminal disclaimer.

(21) Appl. No.: 11/286,875

(22) Filed: Nov. 23, 2005

(65) Prior Publication Data
US 2006/0110452 A1  May 25, 2006

Related U.S. Application Data

(63) Continuation-in-part of application No. 11/106,816, filed on Apr. 15, 2005.

(60) Provisional application No. 60/573,881, filed on May 24, 2004.

(51) Int. Cl.
A61K 9/28 (2006.01)
A61K 9/20 (2006.01)
A61K 31/675 (2006.01)

(52) U.S. Cl. .................. 424/474; 424/465; 424/468; 514/89

(58) Field of Classification Search .................. 424/474
See application file for complete search history.

(56) References Cited

U.S. PATENT DOCUMENTS

| 5,296,475 | A | 3/1994 | Flesch et al. |
| 5,304,377 | A | 4/1994 | Yamada et al. |
| 5,431,920 | A * | 7/1995 | Bechard ................ 424/480 |
| 5,462,932 | A | 10/1995 | Brenner et al. |
| 5,622,721 | A | 4/1997 | Dansereau et al. |
| 5,686,106 | A | 11/1997 | Kelm et al. |
| 5,853,759 | A | 12/1998 | Katdare et al. |
| 6,143,326 | A | 11/2000 | Mockel et al. |
| 6,200,602 | B1 | 3/2001 | Watts et al. |
| 6,248,363 | B1 | 6/2001 | Patel et al. |
| 6,309,663 | B1 | 10/2001 | Patel et al. |
| 6,333,316 | B1 | 12/2001 | Daifotis et al. |
| 6,368,629 | B1 * | 4/2002 | Watanabe et al. ......... 424/482 |
| 6,432,932 | B1 * | 8/2002 | Daifotis et al. ............. 514/108 |
| 6,506,407 | B2 | 1/2003 | Watanabe et al. |
| 6,623,755 | B2 | 9/2003 | Chen et al. |
| 6,676,965 | B1 | 1/2004 | Lulla et al. |
| 6,677,320 | B2 | 1/2004 | Diederich et al. |
| 7,309,698 | B2 | 12/2007 | Boyd et al. |
| 2001/0036475 | A1 | 11/2001 | Chen et al. |
| 2003/0158154 | A1 | 8/2003 | Fleshner-Barak |
| 2003/0203878 | A1 | 10/2003 | Flashner-Barak et al. |
| 2005/0089573 | A1 | 4/2005 | Moeckel et al. |
| 2005/0182028 | A1 | 8/2005 | Chen |
| 2005/0226907 | A1 | 10/2005 | Moneymaker et al. |
| 2005/0260262 | A1 | 11/2005 | Dansereau et al. |
| 2006/0069069 | A1 | 3/2006 | Kajander et al. |
| 2006/0110452 | A1 | 5/2006 | Dansereau et al. |
| 2006/0134190 | A1 | 6/2006 | Kim et al. |
| 2006/0210639 | A1 | 9/2006 | Liversidge et al. |
| 2006/0263355 | A1 | 11/2006 | Quan et al. |
| 2007/0003512 | A1 | 1/2007 | Stockel et al. |
| 2007/0238707 | A1 | 10/2007 | Leonard |

FOREIGN PATENT DOCUMENTS

| BR | 2001-06601 | 9/2003 |
| IN | 2004MU01360 A | 7/2006 |
| JP | 8092102 A2 | 4/1996 |
| WO | WO 93/09785 | 5/1993 |
| WO | WO 93/21907 | 11/1993 |
| WO | WO 97/44017 | 11/1997 |
| WO | WO 98/14196 A1 | 4/1998 |
| WO | WO 99/02539 A1 | 1/1999 |
| WO | WO 00/61111 | 10/2000 |
| WO | 01/12155 A1 | 2/2001 |

(Continued)

OTHER PUBLICATIONS

Lin et al (On the absorption of alendronate in rats. J Pharm Sci. Dec. 1994;83(12):1741-6).*

(Continued)

Primary Examiner—Jake M Vu
(74) Attorney, Agent, or Firm—Kelly L. McDow; Mary Pat McMahon

(57) ABSTRACT

Oral dosage forms of a risedronate comprised of a safe and effective amount of a pharmaceutical composition comprising risedronate, a chelating agent, and, means for effecting delayed release of the risedronate and the chelating agent in the small intestine provide immediate release of the pharmaceutical composition to the small intestine of the mammal subject and pharmaceutically effective absorption of the bisphosphonate with or without food or beverages. The present invention substantially alleviates the interaction between risedronate and food or beverages, which interaction results in the bisphosphonate active ingredient not being available for absorption. The resulting oral dosage form may thus be taken with or without food. Further, the present invention effects delivery of risedronate and the chelating agent to the small intestine, substantially alleviating the upper GI irritation associated with bisphosphonate therapies. These benefits simplify previously complex treatment regimens and can lead to increased patient compliance with bisphosphonate therapies.

30 Claims, No Drawings

FOREIGN PATENT DOCUMENTS

| WO | WO 01/32185 A1 | 5/2001 |
|---|---|---|
| WO | WO 01/52859 | 7/2001 |
| WO | WO 01/76577 | 10/2001 |
| WO | WO 01/82903 | 11/2001 |
| WO | WO 03/002151 | 1/2003 |
| WO | WO 03/007916 | 1/2003 |
| WO | WO 03/051373 A1 | 6/2003 |
| WO | WO 2004/065397 | 8/2004 |
| WO | WO 2005/016872 | 5/2005 |
| WO | WO 2006/019843 | 2/2006 |
| WO | WO 2006/020009 A1 | 2/2006 |

OTHER PUBLICATIONS

Tomita et al (Absorption-enhancing mechanism of EDTA, caprate, and decanoylcarnitine in Caco-2 cells. J Pharm Sci. Jun. 1996;85(6):608-11).*

Ezra, A. et al., Administration routes and delivery systems of bisphosphonates for the treatment of bone resorption, *Drug Delivery Review*, 2000 vol. 42, pp. 175-195.

Mitchell, D. et al., "The effect of dosing regimen on the pharmacokinetics of risedronate", *Br. J. Clin. Pharmoacol.*, 1999, vol. 48, pp. 536-542.

Janner, M. et al., "Sodium EDTA Enhances Intestinal Absorption of Two Bisphosphonates", *Calcified Tissue International*, 1991, vol. 49, pp. 280-283.

Mitchell, D. et al., "Risedronate Gastrointestinal Absorption Is Independent of Site and Rate of Administration", *Pharm. Res.*, 1998, vol. 15, No. 2, pp. 228-232.

Gertz, B.J. et al., "Studies of the oral bioavailability of alendronate", *Clinical Pharmacology & Therapeutics*, 1995, vol. 58, No. 3, pp. 288-298.

Swenson, E.S. et al., "(C) Means to Enhance Penetration (2) Intestinal permeability enhancement for proteins, peptides and other polar drugs: mechanisms and potential toxiciy", *Advanced Drug Deliver Reviews*, 1992, vol. 8, pp. 39-92.

Muranishi, S. "Absorption Enhancers", *Critical Reviews in Therapeutic Drug Carrier Systems*, 1990, vol. 7, No. 1, pp. 1-33.

Lin, J.H. et al., "On the Absorption of alendronate in Rats", *J. of Pharmaceutical Sciences*, 1994, vol. 83, No. 12, pp. 1741-1746.

Tomita, M. et al., "Absorption-enhancing Mechanism of EDTA, Caprate, and Decanoylcarnitine in Caco-2 Cells", *J. of Pharmaceutical Sciences*, 1996, vol. 85, No. 6, pp. 608-611.

Boulenc, X. et al., "Bisphosphonates increase tight junction permeability in the human intestinal epithelial (Caco-2) model", *International J. of Pharmaceutics*, 1995, vol. 123, pp. 13-24.

Green, J.R. et al., "The effect of zoledronate and pamidronate on the intestinal permeability barrier in vitro and in vivo", *International J. of Pharmaceutics*, 1997, vol. 153, pp. 59-66.

Poiger, H. et al., "Compensation of Dietary Induced Reduction of Tetracycline Absorption by Simultaneous Administration of EDTA", *Europ. J. Clin. Pharmacol*, 1978, vol. 14, pp. 129-131.

Nykanen, P. et al., "Citric acid as excipient in multiple-unit enteric-coated tablets for targeting drugs on the colon", *International J. of Pharmaceutics*, 2001, vol. 229, pp. 155-162.

Rowe, R.C. (Ed.), "Edetic Acid", *Handbook of Pharmaceutical Excipients*, 2002, pp. 225-228.

Bronner, F. et al., "Nutritional Aspects of Calcium Absorption", *J. Nutr.*, 1999, vol. 129, pp. 9-12.

Whittaker, P. et al., "Toxicological Profile, Current Use, and Regulatory Issues on EDTA Compounds for Assessing Use of Sodium Iron EDTA for Food Fortification", *Regulatory Toxicology and Pharmacology*, 1993, vol. 18, pp. 419-427.

Watts, P.J. et al., "Colonic Drug Delivery", *Drug Development and Industrial Pharmacy*, 1997 vol. 23, No. 9, pp. 893-913.

Kinget, R. et al., "Colonic Drug Targeting", *J. of Drug Targeting*, 1998, vol. 6, No. 2, pp. 129-149.

Mahe, S. et al., "Gastroileal Nitrogen and Electrolyte Movements after Bovine Milk Ingestion in Humans", *Am. J. Clin Nutr*, 1992, vol. 56, pp. 410-416.

PCT International Search Report dated Dec. 7, 2005.

Simon, Zakelj,, et al., "The effect of clodronate on the integrity and viability of rat small intestine in vitro—a comparison with EDTA," Biological pharmaceutical bulletin, (Jul. 2005) vol. 28, No. 7, pp. 1249-1253.Journal code: 9311984. ISSN: 0918-6158.

U.S. Appl. No. 11/106,816, filed Apr. 15, 2005, Dansereau et al.

U.S. Appl. No. 12/183,336, filed Jul. 31, 2008, Dansereau et al.

U.S. Appl. No. 12/183,359, filed Jul. 31, 2008, Dansereau et al.

Boulenc, X. et al., "Importance of the paracellular pathway for the transport of a new bisphosphonate using the human CACO-2 monolayers model," *Biochemical Pharmacology*, vol. 46, No. 9, pp. 1591-1600. (1993).

Dowty, M. et al. AAPS Annual Meeting, San Francisco, Nov. 19, 1998.

Perez-Millan, Antonio, "Subserosal Eosinophilic Gastroenteritis Treated Efficaciously with Sodium Cromoglycate," *Digestive Diseases and Sciences*, vol. 42, No. 2, Feb. 1997.

Raiman, J. et al., "Effects of various absorption enhancers on transport of clodronate through caco-2 cells," *International Journal of Pharmaceutics*, 2003, vol. 261, pp. 129-136.

* cited by examiner

DOSAGE FORMS OF RISEDRONATE

CROSS REFERENCE TO RELATED APPLICATION

This application is a continuation-in-part of U.S. application Ser. No. 11/106,816, filed Apr. 15, 2005 which claims the benefit of Provisional Application Ser. No. 60/573,881, May 24, 2004

FIELD OF THE INVENTION

The present invention relates to oral dosage forms of risedronate comprised of a safe and effective amount of a pharmaceutical composition comprising a bisphosphonate, a chelating agent for enabling administration of risedronate with food or beverages, means for effecting delayed release of risedronate and the chelating agent in the small intestine, and one or more pharmaceutically-acceptable excipients. The oral dosage forms of the invention provide delivery of the pharmaceutical composition to the small intestine of the mammal subject and provide pharmaceutically effective absorption of risedronate when administered with or without food or beverages. The present invention further relates to a method of treating or preventing diseases characterized by abnormal calcium and phosphate metabolism comprising administering to a human or other mammal in need thereof the oral dosage form described herein.

BACKGROUND OF THE INVENTION

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories:

1. Conditions which are characterized by anomalous mobilization of calcium and phosphate leading to general or specific bone loss or excessively high calcium and phosphate levels in the fluids of the body. Such conditions are sometimes referred to herein as pathological hard tissue demineralization.

2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Essential quantities of cancellous bone are lost, and marrow and bone spaces become larger, resulting in reduced cancellous bone strength. Bone also becomes less dense and fragile. Osteoporosis can be subclassified as senile, drug induced (e.g., adrenocorticoid, as can occur in steroid therapy), disease induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastasis are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

Bisphosphonates tend to inhibit the resorption of bone tissue, which is beneficial to patients suffering from excessive bone loss. However, many of the early bisphosphonates, such as ethane-1,1-diphosphonic acid (EHDP), propane-3-amino-1-hydroxy-1,1-diphosphonic acid (APD), and dichloromethane diphosphonic acid ($Cl_2MDP$), have the propensity of inhibiting bone mineralization when administered at high dosage levels. Although more biologically potent bisphosphonates exist, which can be administered at lower dosage levels (such as 1-hydroxy-2-(3-pyridinyl)-ethylidene-1,1-bisphosphonic acid (risedronate), alendronate, ibandronate, and zoledronate), oral administration of bisphosphonates sometimes results in patient complaints shortly after dosing. These complaints are usually characterized by the patients as heartburn, esophageal burning, pain and/or difficulty upon swallowing, and/or pain existing behind and/or mid-sternum. It is hypothesized that this irritation results from the bisphosphonate tablet adhering to epithelial and mucosal tissues, resulting in the topical irritation thereof. In order to avoid potential upper gastrointestinal irritation, patients taking bisphosphonates are instructed to take their medication with a full glass of water, and to remain upright for at least thirty minutes after taking an oral dose of a bisphosphonate.

It is known that oral doses of bisphosphonates are poorly absorbed (less than 1% of the oral dose) in the gastrointestinal (GI) tract. See Ezra et al., Adv. Drug Del. Rev. 42: 175-95 (2000). Several approaches have been suggested for increasing absorption of oral bisphosphonates throughout the GI tract. These approaches include modifying the permeability properties of the intestinal mucosa (e.g., through the use of absorption enhancers), or altering the physical or chemical properties of the bisphosphonate compounds themselves (e.g., through prodrugs).

While the use of absorption enhancers, such as ethylenediaminetetraacetic acid (EDTA), that increase intestinal permeability at high doses, has been proposed as a means of increasing absorption of oral bisphosphonates, the applicability of EDTA as an agent in human pharmacotherapy has been thought to be "impossible" in light of the effects of EDTA on mucosal integrity. Ezra et al., Adv. Drug Del. Rev. 42: 185 (2000). Still others have concluded that the high amount of EDTA required to effect an increase in GI absorption would exclude the agent as a candidate for use in oral bisphosphonate therapies. See Janner et al., Calcif. Tissue Int. 49: 280-83 (1991).

While the primary site of bisphosphonate absorption is the small intestine, bisphosphonates such as risedronate have similar absorption throughout the small intestine independent of where it was delivered. See Mitchell et al., Pharm Res., Vol. 15, No. 2: 228-232 (1998). Thus targeted delivery of the bisphosphonate alone to the small intestine would not increase absorption or efficacy of the bisphosphonate. However, others have attempted to increase the absorption of bisphosphonates by increasing the permeability of the intestinal mucosa through delivery of microparticles of chelating agents and bisphosphonate to the reported site of absorption (BR2001-006601).

Bisphosphonates such as risedronate and alendronate have been approved by a number of regulatory agencies as being effective in the treatment of various bone pathologies. However, interactions between bisphosphonates and foods and minerals (especially cations like calcium, magnesium, aluminum, and iron-containing foods or supplements) cause less of the bisphosphonate to be available for absorption. For example, in Mitchell et. al., Br. J. Clin. Pharmacol. 48: 536-542 (1999), it was demonstrated that administration of risedronate within 30 minutes of a meal reduced the amount absorbed by 50% compared to administration in the fasting state. In order to reduce this food effect, the labeling of oral bisphosphonate products instruct patients to take their medication at least thirty minutes or in the case of Ibandronate sixty minutes, before the first food of the day, and are instructed to take their calcium supplements at another time of the day, or on a day when they are not taking an oral dose of a bisphosphonate. These dosing instructions can seem complex and inconvenient to the patient, which can lead to poor patient compliance.

There is an ongoing need to develop an oral dosage form of a bisphosphonate which can be taken with or without food or beverages (i.e. has pharmaceutically effective absorption regardless of food or beverage intake), at the preference of the patient, and which does not produce upper gastrointestinal irritation.

It has been found that a pharmaceutical composition comprising risedronate, a sufficient amount of chelating agent to bind the ions and minerals in food, and a means for effecting delayed release of risedronate and the chelating agent in the small intestine is useful in providing an oral dosage form which provides immediate release of risedronate to the small intestine, as well as pharmaceutically effective absorption of risedronate when administered with or without food or beverages. The oral dosage forms of the present invention may be taken with or without food or beverages, thus simplifying the bisphosphonate treatment therapy and leading to increased patient compliance and convenience. Further, the oral dosage forms of the invention provide for delayed release of risedronate and the chelating agent in the small intestine, which may alleviate the upper gastrointestinal irritation experienced with other oral bisphosphonate dosage forms and the need to remain upright for thirty minutes post-dose administration.

SUMMARY OF THE INVENTION

The present invention relates to an oral dosage form of risedronate active ingredient comprising a safe and effective amount of a pharmaceutical composition comprising:
(a) from about 1 mg to about 250 mg risedronate;
(b) from about 10 mg to about 970 mg of a chelating agent; and
(c) a delayed release mechanism to immediately release the risedronate and the chelating agent in the small intestine; wherein such composition is a tablet size of no greater than one gram.

The dosage forms of the present invention provide an immediate release of risedronate and the chelating agent to the small intestine of the mammal subject and pharmaceutically effective absorption of risedronate active ingredient when administered with or without food or beverages.

The present invention substantially alleviates the interaction between risedronate and food, which interaction results in decreased absorption of risedronate. The resulting novel oral dosage form may thus be taken with or without food or beverages, which simplifies previously complex treatment regimens and can lead to increased patient compliance with bisphosphonate therapies and if the patients are compliant their disease can be better treated. The invention further alleviates the potential for upper gastrointestinal irritation associated with non-delayed, immediate release oral dosage forms of bisphosphonates, by delaying release of the bisphosphonate active ingredient until the bisphosphonate and the chelating agent reach the small intestine.

The present invention further relates to a method of treating or preventing diseases characterized by abnormal calcium and phosphate metabolism comprising administering to a human or other mammal in need thereof the oral dosage form described herein.

The invention further relates to a kit comprising one or more oral dosage forms of the present invention and means for facilitating compliance with methods of this invention.

DETAILED DESCRIPTION OF THE INVENTION

Definitions and Usage of Terms

The term "immediate release" as used herein means dissolution of the core tablet in less than 60 minutes, when measured by standard USP definitions. For example, the USP specifies that all tablets and capsules are subject, to a general dissolution standard of not less than 75% of the core content is dissolved in not more than 45 minutes in 900 mL of water, using the apparatus, procedures, and interpretation presented in the United States Pharmacopeia chapter, Dissolution, page 959. For this purpose, 75% is Q, and conformance is demonstrated with either one of Apparatus 1 at 100 rpm or Apparatus 2 at 50 rpm."

The terms "continuous" or "continuously," as used herein, mean at regular specified intervals. For example, a continuous schedule according to a dosing regimen of once weekly means that the active is given one time per week for an unspecified period of time or for as long as treatment is necessary.

The term "delayed release or delayed delivery," as used herein, refers to formulating the pharmaceutical composition comprising risedronate and the chelating agent so that their release will be accomplished at some generally predictable location in the small intestine.

The term "nutrient," as used herein, means any nutritional or dietary supplement including but not limited to vitamins, minerals, amino acids, herbs or other botanicals, or concentrates, metabolites, constituents, extracts, or combinations of the same.

The term "pharmaceutical composition," as used herein, means an oral dosage form comprised of a safe and effective amount of risedronate and one or more pharmaceutically-acceptable excipients including at least one chelating agent. The pharmaceutical compositions described herein are comprised of from 0.5% to 75%, preferably from 1% to 40% of risedronate and from 25% to 99.5%, preferably from 60% to 99% of pharmaceutically-acceptable excipients including at least one chelating agent.

The term "safe and effective amount," as used herein, means an amount of a compound or composition high enough to significantly positively modify the symptoms and/or condition to be treated, but low enough to avoid serious side effects (at a reasonable risk/benefit ratio), within the scope of sound medical judgment. The safe and effective amount of active ingredient for use in the method of the invention herein will vary with the particular condition being treated, the age and physical condition of the patient to be treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically effective absorption" as used herein means an amount of a chelating compound high enough to significantly bind the metal ions and minerals in food but low enough not to significantly alter absorption of risedronate as compared to absorption in the fasted state. That is, absorption is similar with or without food. Given the high variability of bisphosphonate absorption, fed exposure within about 50% of fasting exposure is expected to be pharmaceutically effective absorption.

The term "oral dosage form," as used herein, means any pharmaceutical composition intended to be delivered or released to the small intestine of a human or other mammal via the mouth of said human or other mammal. For the purposes of the present invention, the delivered form can be in the form of a compressed tablet containing granules or particles of risedronate and a chelating agent The term "unit dose" or "unit dosage" means a dosage form containing an amount of pharmaceutical active or nutrient suitable for administration in one single dose, according to sound medical practice. The present invention is particularly useful for the administration of unit doses in the form of tablets and capsules.

The term "gastrointestinal tract" or "GI tract," as used herein, relates to the alimentary canal, i.e., the musculomembranous tube about thirty feet in length, extending from the mouth to the anus. The term "upper gastrointestinal tract," as used herein, means the buccal cavity, the pharynx, the esophagus, and the stomach. The term "lower gastrointestinal tract," as used herein, means the small intestine and the large intestine.

The term "small intestine," as used herein, means the part of the small intestine consisting of just distal to the stomach, including the duodenum, the jejunum, and the ileum, i.e., that portion of the intestinal tract just distal to the duodenal sphincter of the fundus of the stomach and proximal to the large intestine. The term "large intestine," as used herein, means the part of the lower gastrointestinal tract including the ascending colon, the transverse colon, the descending colon, the sigmoid colon, and the rectum Risedronate The terms "bisphosphonate" and "diphosphonate," as used herein, include acids, salts, esters, hydrates, polymorphs, hemihydrates, solvates, and derivatives thereof. The bisphosphonates of the present invention include those forms of 1-hydroxy-2-(3-pyridinyl)-ethylidene-1,1-bisphosphonic acid (risedronate) as described in U.S. Pat. No. 5,583,122, to Benedict et al., issued Dec. 10, 1996; U.S. Pat. No. 6,410,520 B2, to Cazer et al., issued Jun. 25, 2002

Non-limiting examples of salts useful herein include those selected from the group consisting of alkali metal, alkaline metal, ammonium, and mono-, di-, tri-, or tetra-$C_1$-$C_{30}$-alkyl-substituted ammonium. Preferred salts are those selected from the group consisting of sodium, potassium, and ammonium salts.

The amount of risedronate contained in the oral dosage forms of the present invention will depend on the particular risedronate form selected and the continuous dosing schedule upon which the risedronate is dosed to the patient. Continuous dosing schedules of daily, weekly, twice monthly, three times per month, and once monthly are non-limiting examples of dosing regimens suitable for use with the oral dosage forms of the present invention. The terms "three times per month" or "thrice monthly" mean that an oral dosage form is administered thrice, i.e., three times, during a monthly calendar period. In a thrice monthly schedule, the oral dosage forms may be administered on three consecutive days, or once about every nine to eleven days. The terms "twice per month" or "twice monthly" mean that an oral dosage form is administered twice, i.e., two times, during a monthly calendar period. In a twice monthly regimen, the oral dosage forms may be administered on consecutive days or once about every fourteen to sixteen days. The terms "monthly" or "once monthly" mean that an oral dosage form is administered once, i.e., one time during a monthly calendar period, that is, about every 28 to 31 days.

Mixed nomenclature is currently in use by those of ordinary skill in the art, for example reference to a specific weight or percentage of a bisphosphonate active ingredient is on an anhydrous monosodium salt basis for risedronate. For the present invention, the phrase "about 35 mg of risedronate, pharmaceutically acceptable salts thereof, and mixtures thereof, on an anhydrous monosodium salt basis" means that the amount of the risedronate compound selected is calculated based on about 35 mg of anhydrous risedronate monosodium salt.

Generally, the oral dosage forms of the present invention will contain from about 1 mg to about 250 mg of risedronate on a risedronate anhydrous monosodium salt basis. A daily oral dosage form of the present invention contains from about 1 mg to about 10 mg risedronate on a risedronate anhydrous monosodium salt basis. A weekly oral dosage form contains from about 10 to about 70 mg risedronate on a risedronate anhydrous monosodium salt basis, preferably from 15 to about 55 mg risedronate, more preferably from about 35 mg to about 50 mg risedronate. A twice monthly oral dosage form contains from about 20 to about 120 mg risedronate, preferably about 75 mg to about 90 mg risedronate on a risedronate anhydrous monosodium salt basis. An oral dosage form that is administered three times per month contains from about 15 to about 90 mg risedronate, preferably about 50 mg to about 75 mg risedronate, on a risedronate anhydrous monosodium salt basis. A monthly oral dosage form contains from about 50 to about 280 mg risedronate, preferably from about 100 to about 250 mg risedronate, and more preferably about 150 to about 200 mg risedronate on a risedronate anhydrous monosodium salt basis. In one embodiment of the invention the dosage form contains about 100% of the effective amount of the risedronate as equivalent non-chelating agent containing, non-delayed, immediate released risedronate tablets. In yet another embodiment of the invention the dosage form is about 145% of the effective amount of the risedronate as equivalent non-chelating agent containing, non-delayed, immediate released risedronate tablets.

Chelating Agent

The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology (4th ed. 2001).

In homogeneous dilute solutions, the equilibrium constant for the formation of the complex from the solvated metal ion (e.g., calcium) and the chelating agent in its fully dissociated form is called the formation or stability constant, K. The practical significance of formation constants is that a high log K value means a large ratio of chelated to unchelated (or free) metal ion, when equivalent amounts of metal ion and chelating agent are present. Higher ratios (or difference if K is expressed in log units) of the chelating agent and the bisphosphonate complexation constants are preferred in order to have nearly all of the metal ion complexed to the chelating agent instead of the bisphosphonate. For example, for equal molar amounts of both bisphosphonate and the chelating agent, in order for the metal ions to be 99% complexed to the chelating agent, the chelating agent must have a log K which is at least 4 units higher than the bisphosphonate-metal ion complex. The other technique which can be used to favor the chelating agent-metal ion complex over that of the bisphosphonate-metal ion complex is to add a molar excess of the chelating agent which relies on the law of mass action to favor formation of the chelating agent-metal ion complex.

Although pH and solution concentration can affect the formation constant, in general, the log K of the chelating agent is preferably at least equal to that of the bisphosphonate. In other instances the log K of the chelating agent is 2 to 5 units higher than that of the bisphosphonate. In other instances, the chelating agent is present at a molar excess to that of the bisphosphonate. The chelating agent in such instances is present in at least a 2:1 molar ratio of the chelating agent to bisphosphonate.

The chelating agent and the form it is administered is at least 50% as soluble in water as risedronate. In other instances the chelating agent and the form it is administered may have a solubility comparable to or greater than that of risedronate.

In one embodiment, the chelating agent is selected from the group consisting of sodium or disodium EDTA, citric acid, malic acid, tartaric acid, lactic acid, adipic acid, succinic acid, lysine, sodium hexametaphosphate, and combinations thereof. In another embodiment, the chelating agent is sodium of disodium EDTA, citric acid, or sodium hexametaphosphate.

The amount of chelating agent present in the oral dosage form of the present invention will depend on the particular chelating agent or agents (i.e. mixtures of chelating agents) selected, the amount of bisphosphonate active ingredient present in the oral dosage form, and the specific portion of the small intestine where delivery and release of the chelating agent and/or bisphosphonate active ingredient is desired. After the ingestion of milk, it has been shown in the art that the concentration of calcium decreases over the length of the lower GI tract, beginning with the small intestine and proceeding through to the end of the small intestine. Mahe, J. et al., *Gastroileal nitrogen and electrolyte movements after bovine milk ingestion in humans*, Am. J. Clin. Nutr. 56: 410-16 (1992).

The concentration of calcium in the stomach is approximately 10-fold higher than that of the concentration in the jejunum and approximately 40 times that in the ileum. Thus, if the risedronate and chelating agent were released in the stomach (with food), the amount of chelating agent of the present invention would be insufficient to overcome the effect of calcium on drug absorption. The concentration of calcium in the jejunum and ileum are lower and by targeting release of the dosage form in these regions where the amount of calcium is lower, the chelating agent is more effective at binding most of all of the calcium than if released in the stomach. It is also desirable not only to have targeted release of the tablet in the small intestine but after the coating dissolves the chelating agent and risedronate from the core tablet releases in an immediate release fashion. This maximizes the local concentration of the chelating agent in relationship to that of the calcium in the small intestine. Slow or prolonged delivery of the chelating agent in the small intestine does not achieve the desired local concentration of the chelating agent and this type of delivery will not overcome the food effect.

Generally, the oral dosage forms of the present invention will contain a safe and effective amount of a chelating agent suitable for achieving the desired chelating effect, that is, chelating the residual metal ions that are present in the gastrointestinal tract from food at the site of delivery without significantly affecting the absorption of the bisphosphonate had no food been present. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is disodium EDTA, the preferred range is from about 55 mg to about 500 mg, preferably from about 75 mg to about 250 mg per unit dose. When the chelating agent is citric acid, the preferred range is from about 100 mg to about 970 mg, preferably from about 250 mg to about 500 mg per unit dose.

Delayed Delivery to the Small Intestine

The ultimate site of and/or the rate of delivery in the small intestine can be satisfactorily controlled by one skilled in the art, by manipulating any one or more of the following:
 (a) the active ingredient proper;
 (b) the type and level of disintegrant;
 (c) the type of coating, the type and level of excipients added to the coating and the concomitant desirable thickness and permeability (swelling properties) of the coating;
 (d) the time dependent conditions of the coating itself and/or within the coated tablet, particle, bead, or granule;
 (e) the particle size of the granulated active ingredient;
 (f) the pH dependent conditions of the coating itself and/or within the coated tablet, particle, bead, or granule;
 (g) the particle size or solubility of the chelating agent;
 (h) the dissolution rate of the coating;
 (i) size or shape of the tablet.

In addition the pharmacodynamic effect of the tablets, after multiple dosing, should be within at least 75% of the comparable immediate release tablet.

Delayed Release in the Small Intestine

A human or other mammal suffering from diseases or disorders involving calcium and phosphate metabolism can be successfully treated by the delivery of risedronate to the small intestine of said human or other mammal. The novel dosage forms described herein effect an immediate release to the small intestine, and prohibit the undesired release of risedronate in the mouth, pharynx, esophagus, and/or stomach, thereby prohibiting the erosion, ulceration, or other like irritation of the epithelial or mucosal layers of these tissues.

The chelant and risedronate are released rapidly and as close to simultaneously as possible. This causes the local concentration of chelating agent to be higher in relationship to the metal ions in the food. The higher local concentration of chelating agent in the environment where the active is released may more effectively complex the metals in the food and facilitate absorption of the bisphosphonate. This can be conveniently achieved from a single tablet.

Various means for targeting release of risedronate and the chelating agent in the small intestine are suitable for use in the present invention. Non-limiting examples of means for delivery to the small intestine include pH triggered delivery systems and time dependent delivery systems.

pH Triggered Delivery Systems

One embodiment of the present invention involves coating (or otherwise encapsulating) the risedronate and the chelating agent(s) with a substance which is not broken down, by the gastrointestinal fluids to release the risedronate and the chelating agent until a specific desired point in the intestinal tract is reached. In one embodiment, delayed release of the pharmaceutical composition is achieved by coating the tablet, capsule, particles, or granules, of the risedronate and the chelating agent with a substance which is pH dependent, i.e., broken down or dissolves at a pH which is generally present in the small intestine, but not present in the upper GI tract (i.e., the mouth, buccal cavity, pharynx, esophagus, or stomach) or lower GI tract.

In some cases, it may be desirable that the risedronate and the chelating agent are released at a particular location in the small intestine. In other cases, it may be desirable to release the risedronate and the chelating agent independently at different locations within the small intestine. For example, it may be desirable to release the chelating agent in the, jenunum and the risedronate in the.ileum When targeted release of the risedronate and the chelating agent together or separately in particular locations within the small intestine is desired, the selection of the coating material and/or the method of coating or otherwise combining the risedronate and the chelating agent with the selected coating material or other pharmaceutically-acceptable excipients may be varied or altered as is described herein, or by any method known to one skilled in the art.

Solubility, acidity, and susceptibility to hydrolysis of the different risedronate active ingredients, such as acid addition salts, salts formed with the phosphonic group (e.g., alkali metal salts, alkaline earth metal salts, etc.), and esters (e.g., alkyl, alkenyl, aryl, arylalkyl) may be used as guidelines for the proper choice of coating. In addition, suitable pH conditions might be established within the coated tablets, particles, or granules by adding a suitable buffer to the active ingredient in accordance with the desired release pattern.

One embodiment of the present invention is delivered to the small intestine utilizing a pH dependent enteric coating material made from a partly methyl esterified methacrylic acid polymer. The oral dosage form can be in the form of an enteric coated compressed tablet made of granules or particles of active ingredient.

Any enteric coating which is insoluble at a pH below 5.5 (i.e., that generally found in the mouth, pharynx, esophagus, and stomach), but soluble between about pH 5.5 and about pH 6.5 (i.e., that present in the small intestine) can be used in the practice of the present invention. Accordingly, when it is desired to effect delivery of the bisphosphonate and the chelating agent to the small intestine, any enteric coating is suitable which is wholly- or partially-insoluble at a pH below 5.5 and soluble at about a pH 5.5 to about pH 6.5.

The enteric coating must be applied to the compressed tablet, or capsule (e.g., gelatin, starch, or hydroxypropylmethylcellulose) in a sufficient thickness so that the entire coating does not dissolve in gastrointestinal fluids at a pH below 5.5, but does dissolve at a pH above about 5.5 and below pH about 6.5. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present invention to achieve delivery of the bisphosphonate and chelating agent to the small intestine. The coating chosen must be compatible with the particular risedronate active ingredient selected. The preferred polymers for use in the present invention are anionic carboxylic polymers. It is particularly preferred that the polymers are acrylic polymers, more preferably partly methyl-esterified methacrylic acid polymers, in which the ratio of free anionic carboxyl groups to ester groups is about 1:1

A particularly suitable methacrylic acid copolymer is Eudragit L®, particularly Eudragit L 30 D-55® and Eudragit L 100-55®, manufactured by Röhm Pharma GmbH and Co. KG, Darmstadt, Germany. In Eudragit L 30 D-55®, the ratio of free carboxyl groups to ester groups is approximately 1:1. Further, said copolymer is known to be insoluble in GI fluids having a pH below 5.5, generally 1.5-5.5, i.e., that generally present in the fluid of the upper GI tract, but readily soluble at pH above 5.5, i.e., that generally present in the fluid of the small intestine.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, acteyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness must be sufficient to ensure that the oral dosage form remains essentially intact until the desired site of delivery in the small intestine is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated. In an embodiment of the invention the tablets are compressed and the tablet is enteric coated.

Suitable enteric coating materials include Eudragit L-100®, Eudragit L 30 D-55®, cellulose acetate phthalate, shellac, or any enteric coating material that dissolves at about pH 5.5 to about 6.5. The enteric coating is applied using various spray techniques known to one skilled in the art. The enteric coating may further comprise one or more pharmaceutically-acceptable excipients including, but not limited to, talc, triethyl citrate, polyethylene glycol, Tween 80® (polyoxyethylene sorbitan monooleate, available from Sigma Chemical CO., St. Louis, Mo.), castor oil. The enteric coating is applied to the tablet core to provide a weight gain of 2.5% to 40%.

The tablet core comprises a bisphosphonate active ingredient, a chelating agent, and may contain one or more pharmaceutically-acceptable excipients. Suitable excipients include, but are not limited to, crystalline cellulose, lactose, calcium hydrogen phosphate, polyvinylpyrrolidone, magnesium stearate, sucrose, starch, magnesium oxide, sodium starch glycolate and sodium lauryl sulfate.

Time Dependent Delivery Systems

In another embodiment of the invention, delivery of the risedronate and the chelating agent to the small intestine is achieved through the use of a time dependent delivery system. Given established transit times after gastric emptying, drug and/or chelating agent release can be targeted to the various segments of the small intestine. Approaches to time dependent delivery systems suitable for use in the present invention include, but are not limited to, such devices as the Pulsincap™ (Scherer DDS, Strathclyde, U.K.), the Time Clock™

(Zambon Group, Milan, Italy), and SyncroDose™ (Penwest, Patterson, N.Y.), as well as various coatings which degrade over time to release tablet contents such as hydroxypropylmethylcellulose, hydroxypropylcellulose, or any suitable hydrogel.

In one embodiment of the invention, the time-dependent device Pulsincap™ is used to target delivery of the active ingredient and the chelating agent to the small intestine. The active ingredient and other excipients, including the chelating agent, are contained inside the Pulsincap™ water-insoluble capsule by means of a hydrogel plug which is covered by a water-soluble cap. The entire dose form is optionally coated in an enteric-coating material to protect the dose form from degradation while in transit through the upper GI tract. When the patient swallows the Pulsincap™ dosage form, the water-soluble cap dissolves and exposes the hydrogel plug to gastric and/or intestinal fluids. The hydrogel cap then swells, and eventually pops out of the capsule body, thus releasing the capsule contents. Release of the capsule contents can be targeted to specific regions of the small intestine by modifying the hydrogel plug properties. Watts, Peter J. & Illum, Lisbeth, Drug Dev. and Indus. Pharm., 23(9): 893-917 (1997).

In one embodiment of the invention, a time dependent coating is applied over a compressed tablet and then an enteric coating is applied over the time dependent coating. This is used to target delivery of the active ingredient and the chelating agent to the small intestine. The active ingredient and other excipients, including the chelating agent, are contained inside the core tablet. The entire dose form is coated with a time dependent coating and then an enteric coating. The enteric-coating material is to protect the dose form from degradation while in transit through the upper GI tract. When the patient swallows the dosage form the enteric coating dissolves after the dosage form leaves the stomach and then the core tablet starts to swell. Eventually, at a predetermined time in the small intestine fluids, the time dependent coating will rupture and releases the contents of the core tablet in the small intestine. Release of the core tablet contents can be targeted to specific regions of the small intestine by modifying the core tablet, time dependent coating and/or the enteric coating.

Pharmaceutically-acceptable Excipients

Pharmaceutically-acceptable excipients include, but are not limited to, polymers, resins, plasticizers, fillers, lubricants, diluents, binders, disintegrants, solvents, co-solvents, surfactants, buffer systems, preservatives, sweetener agents, flavoring agents, pharmaceutical-grade dyes or pigments, chelating agents, viscosity agents, and combinations thereof. Pharmaceutically-acceptable excipients can be used in any component in making the oral dosage form, i.e. core tablet or coating.

Flavoring agents and dyes and pigments among those useful herein include but are not limited to those described in Handbook of Pharmaceutical Excipients (4th Ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, simethicone emulsion, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, (Röhm Pharma GmbH and Co. KG, Darmstadt, Germany), and Acryl-EZE® and Sureteric® (Colorcon, Inc., West Point, Pa.).

Suitable lubricants include, but are not limited to, magnesium stearate, stearic acid, and talc.

Methods of Use

The present invention further relates to a method of treating or preventing diseases characterized by abnormal calcium and phosphate metabolism comprising administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, and other inflammatory conditions which predispose involved tissue to deposition of calcium phosphates.

The oral dosage forms of the present invention are suitable for administration to a patient according to a continuous dosing interval of daily, weekly, three times per month, twice monthly, and monthly.

Kits

The present invention further comprises kits that are particularly useful for administering the oral dosage forms described herein according to a continuous dosing schedule of daily, weekly, three times per month, twice monthly, or monthly. Such kits comprise one or more oral dosage forms comprising risedronate and a chelating agent and a means for facilitating compliance with methods of this invention. Such kits provide a convenient and effective means for assuring that the subject to be treated takes the appropriate oral dosage form in the correct dosage and in the correct manner. The compliance means of such kits includes any means which facilitates administering the active according to a method of this invention. Such compliance means includes instructions, packaging, and dispensing means, and combinations thereof. The kits can also comprise a means for aiding the memory, including but not limited to a listing of the days of the week, numbering, illustrations, arrows, Braille, calendar stickers, reminder cards, or other means specifically selected by the patient. Examples of packaging and dispensing means are well known in the art, including those described in U.S. Pat. No. 4,761,406, Flora et al., issued Aug. 2, 1988; and U.S. Pat. No. 4,812,311, Uchtman, issued Mar. 14, 1989.

Optionally, the kits can comprise at least one oral dosage form comprising a risedronate and a chelating agent and at least one oral dosage form of an accompanying nutrient. Preferred nutrients are calcium and/or vitamin D. Oral forms of calcium suitable for use in the present invention include capsules, compressed tablets, chewable tablets, and the like. Typical salt forms of calcium suitable for use in the present invention include but are not limited to calcium carbonate, calcium citrate, calcium malate, calcium citrate malate, calcium glubionate, calcium gluceptate, calcium gluconate, calcium lactate, dibasic calcium phosphate, and tribasic calcium phosphate. In one embodiment, kits of the present invention may include tablets comprising 400 mg to 1500 mg calcium.

The term "vitamin D," as used herein, refers to any form of vitamin D that may be administered to a mammal as a nutrient. Vitamin D is metabolized in the body to provide what is often referred to as "activated" forms of vitamin D. The term "vitamin D" can include activated and non-activated forms of vitamin D, as well as precursors and metabolites of such forms. Precursors of these activated forms include vitamin $D_2$ (ergocalciferol, produced in plants) and vitamin $D_3$ (cholecalciferol, produced in skin and found in animal sources and used to fortify foods). Vitamins $D_2$ and $D_3$ have similar biological efficacy in humans. Non-activated metabolites of vitamins $D_2$ and $D_3$ include hydroxylated forms of vitamins $D_2$ and $D_3$. Activated vitamin D analogs cannot be administered in large doses on an intermittent schedule, due to their toxicity in mammals. However, non-activated vitamin $D_2$, vitamin $D_3$, and their metabolites may be administered in larger doses than "active" forms of vitamin D on an intermittent basis, without toxicity. In one embodiment, kits of the present invention may include tablets comprising 100 IU to 10,000 IU of vitamin D.

In another embodiment, kits of the present invention may include one or more nutrient tablets comprising both calcium and vitamin D. In a further embodiment, the unit dose of nutrient comprises about 600 mg calcium and about 400 IU vitamin D.

The following non-limiting examples illustrate the formulations, processes, and uses of the present invention.

EXAMPLES

Example I

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
|---|---|
| Eudragit L 30 D-55 ® (wet basis) (manufactured by Röhm Pharma GmbH and Co. KG, Darmstadt, Germany) | 143.3 mg |
| Triethylcitrate | 6.45 mg |
| Talc | 21.5 mg |
| Red Iron Oxide | 0.22 mg |
| Simethicone emulsion (30%) | 0.43 mg |
| Polysorbate 80 | 0.43 mg |
| Purified Water | 307.7 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 30% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 35 mg risedronate tablets, each tablet weighing 240 mg and each containing:

| Active Ingredients: | |
|---|---|
| Risedronate Sodium | 35 mg* |
| Chelant: | |
| Disodium EDTA | 100 mg |
| Excipients | |
| Microcrystalline cellulose | 85.8 mg |
| Sodium starch glycolate | 6 mg |
| Stearic acid | 12 mg |
| Magnesium stearate | 1.2 mg |

*This amount is calculated on a risedronate anhydrous monosodium salt basis.

Tablets having the composition set forth above are prepared as follows:

The risedronate sodium, edetate disodium, sodium starch glycolate, and microcrystalline cellulose are passed through a mill and added to a blender equipped with an intensifier bar. The mixture is blended for approximately ten minutes with the intensifier bar on. The stearic acid and magnesium stearate are screened and added to the blender. The blend is mixed for approximately 3 minutes with the intensifier bar off. The blend is compressed into tablets using a suitable tablet press.

Example II

Enteric-Coated Tablets Containing Risedronate and EDTA

Enteric-coated tablets containing risedronate sodium are prepared as described below, using a similar method set forth in Example I.

A coating composition is prepared from a lacquer containing the following excipients, per tablet:

| Ingredients: | |
|---|---|
| Acryl-EZE (manufactured by Colorcon, Inc., West Point, Pa.) dry solids | 200 mg |
| Purified Water | 950 mg |

A coating weight of 40% weight gain is applied by conventional pan coating to tablets containing 150 mg risedronate and 75 mg EDTA so that oval tablets, each weighing 500 mg, result. The composition of each tablet is as follows:

| Active Ingredients: | |
| --- | --- |
| Risedronate Sodium | 150 mg* |
| Chelant: | |
| Disodium EDTA | 75 mg |
| Excipients | |
| Mannitol | 100 mg |
| Starch 1500 | 159 mg |
| Silicon Dioxide | 1 mg |
| Stearic acid | 15 mg |

*This amount is calculated on a risedronate anhydrous monosodium salt basis.

Example III

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
| --- | --- |
| Eudragit L 30 D-55 ® (wet basis) | 51.37 mg |
| (manufactured by Röhm Pharma GmbH and Co. KG, Darmstadt, Germany) | |
| Triethylcitrate | 1.54 mg |
| Talc | 11.56 mg |
| Red Iron Oxide | 0.02 mg |
| Simethicone emulsion (30%) | 0.05 mg |
| Polysorbate 80 | 0.15 mg |
| Purified Water | 79.21 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of approximately 10% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 35 mg risedronate tablets, each tablet weighing 290 mg and each containing:

| Active Ingredients: | |
| --- | --- |
| Risedronate Sodium | 35 mg* |
| Chelant: | |
| Disodium EDTA | 100 mg |
| Excipients: | |
| ProSolv SMCC 90 | 131.8 mg |
| Stearic Acid | 14.5 mg |
| Sodium Starch Glycolate | 7.25 |
| Magnesium stearate | 1.5 mg |

*This amount is calculated on a risedronate anhydrous monosodium salt basis.

Tablets having the composition set forth above are prepared as follows:

The risedronate sodium, edetate disodium, sodium starch glycolate, ½ of the ProSolv SMCC90, ½ of the stearic acid and ½ of the magnesium stearate are passed through a mill and added to a blender equipped with an intensifier bar. The mixture is blended for approximately twenty minutes with the intensifier bar on and then chilsonated and milled. The remaining ProSolv SMCC90, and stearic acid are added and mixed for another 10 minutes. The remaining magnesium stearate is screened and added to the blender with the granulation. The blend is mixed for approximately 3 minutes with the intensifier bar off. The blend is compressed into tablets using a suitable tablet press.

Example IV

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
| --- | --- |
| Eudragit L 30 D-55 ® (wet basis) | 66.10 mg |
| (manufactured by Röhm Pharma GmbH and Co. KG, Darmstadt, Germany) | |
| Triethylcitrate | 1.99 mg |
| Talc | 14.87 mg |
| Yellow Iron Oxide | 0.02 mg |
| White Chromatone | 0.07 |
| Simethicone emulsion (30%) | 0.06 mg |
| Polysorbate 80 | 0.20 mg |
| Purified Water | 101.89 mg |

The enteric coating is prepared using the following method:

A pigment suspension is prepared by adding polysorbate 80, ground ferric oxide, White Chromatone, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of approximately 9% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 50 mg risedronate tablets, each tablet weighing 414.3 mg and each containing:

| Active Ingredients: | |
|---|---|
| Risedronate Sodium | 50 mg* |
| Chelant: | |
| Disodium EDTA | 142.9 mg |
| Excipients: | |
| ProSolv SMCC 90 | 188.3 mg |
| Stearic Acid | 20.7 mg |
| Sodium Starch Glycolate | 10.4 |
| Magnesium stearate | 2.0 mg |

*This amount is calculated on a risedronate anhydrous monosodium salt basis.

Tablets having the composition set forth above are prepared as follows:

The risedronate sodium, edetate disodium, sodium starch glycolate, ½ of the ProSolv SMCC90, ½ of the stearic acid and ½ of the magnesium stearate are passed through a mill and added to a blender equipped with an intensifier bar. The mixture is blended for approximately twenty minutes with the intensifier bar on and then chilsonated and milled. The remaining ProSolv SMCC90, and stearic acid are added and mixed for another 10 minutes. The remaining magnesium stearate is screened and added to the blender with the granulation. The blend is mixed for approximately 3 minutes with the intensifier bar off. The blend is compressed into tablets using a suitable tablet press.

Example V

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
|---|---|
| Eudragit L 30 D-55 ® (wet basis) (manufactured by Röhm Pharma GmbH and Co. KG, Darmstadt, Germany) | 150 mg |
| Triethylcitrate | 10 mg |
| Talc | 30 mg |
| Black Iron Oxide | 0.1 mg |
| Purified Water | 250 mg |

The enteric coating is prepared using the following method:

The talc and black iron oxide are added to a portion of purified water and mixed until uniform. The triethylcitrate is added with continuous mixing. The resulting pigment suspension is next passed through a screen or a suitable mill to break up agglomerates. The Eudragit L 30 D-55® is screened and then added to a suitable vessel and diluted with a portion of the purified water. The pigment suspension is then added to the diluted Eudragit suspension and mixed until uniform.

In a suitable coating pan, the compressed tablets (10 kg) containing risedronate and EDTA, described below, are warmed to about 30-35° C. The enteric coating suspension is sprayed onto the tablets at approximately 30 grams per minute. When the spray cycle is completed, the temperature is reduced and the tablets are removed and dried at 30-35° C. for approximately 1 hour.

A coating weight gain of 35% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 5 mg risedronate tablets, each tablet weighing 240 mg and each containing:

| Active Ingredients: | |
|---|---|
| Risedronate sodium | 5.0 mg* |
| Chelant: | |
| Disodium EDTA | 75.0 mg |
| Excipients | |
| Microcrystalline cellulose | 149.5 mg |
| Sodium starch glycolate | 9 mg |
| Stearic acid | 1.5 mg |

*This amount is calculated on a risedronate anhydrous monosodium salt basis.

Tablets having the composition set forth above are prepared as follows:

The tablets are prepared by sieving the risedronate active ingredient and the EDTA with ½ of the microcrystalline cellulose into a twin shell blender. The blend is then mixed until uniform. Then, ½ of the stearic acid is added and the blend is mixed further. The blend is then is roller compacted and milled. The remaining microcrystalline cellulose and sodium starch glycolate are added and mixed until uniform.

The remaining stearic acid is then added and mixed until adequate lubrication is achieved. Tablets are then compressed on a rotary tablet press.

Example VI

Time Dependent and Enteric Coated Tablets Containing Risedronate and Sodium Citrate Time Dependent and Enteric Tablets containing risedronate and sodium citrate are made by preparing a two layer coating composition and compressed tablets containing risedronate and sodium citrate and then applying said coating composition to said tablets.

The first layer (Time Dependent Coating Layer) coating composition is prepared in the form of a polymer containing the following excipients, per tablet:

A. Acid Soluble Coating Layer

| Ingredients: | |
|---|---|
| Ethylcellulose | 40.0 mg |
| Dibuty Sebacate | 8 mg |
| Toluene | 250 mg |
| Ethyl Alcoholc | 70 mg |

The acid soluble coating is prepared using the following method:

A solution is prepared by adding the ethylcellulose to approximately two-thirds of the toluene:ethyl alcohol mixture while mixing. The solution is mixed for at least two hours. The dibuty sebacate is added and mixed for an additional two hours. The resulting coating solution is screened and mixed throughout the coating process.

B. Enteric Coating Suspension

| Ingredients: | |
|---|---|
| Eudragit L 30 D-55 ® (wet basis) (manufactured by Röhm Pharma GmbHand Co. KG, Darmstadt, Germany) | 150 mg |
| Triethyl citrate | 6.0 mg |
| Talc | 15.0 mg |
| Red Iron Oxide | 0.25 mg |
| Purified Water | 260 mg |

The enteric coating is prepared using the following method:

A pigment suspension is prepared by adding ground ferric oxide, and talc to approximately two-thirds of the purified water while mixing. The suspension is mixed for at least two hours. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process.

The compressed tablets are transferred to the coating pan and preheated with occasional jogging. The compressed tablets are coated with the Time Dependent Coating then with the Enteric Coating Suspension using a typical pan coating process until the required quantity of coating solution has been applied. Tablets are then cooled and collected in suitable containers.

A coating weight gain of 10% for the Time Dependent Coating and 13% Enteric Coating (total solids compared to that of the core tablet weight) is applied by spraying the above composition (A and B) onto compressed tablets containing risedronate and sodium citrate prepared in Part C below.

C. Compressed Tablets Containing Risedronate and Sodium Citrate

The Acid Soluble Coating and the Enteric Coating suspension prepared in Part A and B above is sprayed onto 5 mg risedronate tablets, each tablet weighing 500 mg and each containing:

| Active Ingredients: | |
|---|---|
| Risedronate Sodium | 5 mg* |
| Chelant: | |
| Sodium Citrate | 250 mg |
| Excipient | |
| Microcrystalline Cellulose | 109.5 mg |
| Croscarmellose Sodium | 25.0 mg |
| Mannitol | 100 mg |
| Magnesium stearate | 0.5 mg |
| Polyvinylpyrrolidone | 10 mg |
| Purified Water | 100.0 mg |

*This amount is calculated on a risedronate anhydrous monosodium salt basis.

Tablets having the composition set forth above are prepared as follows:

The risedronate sodium, sodium citrate, microcrystalline cellulose, croscarmellose sodium, mannitol and polyvinylpyrrolidone are passed through a mill and added to a blender equipped with an intensifier bar. The mixture is blended for approximately ten minutes with the intensifier bar on and granulated with purified water for 15 minutes. The mixture is dried overnight at 30° C., passed through a mill. The magnesium stearate is screened and added to the blender. The blend is mixed for approximately 3 minutes with the intensifier bar off. The blend is compressed into tablets using a suitable tablet press.

Example VII

Time Dependent Delivery Tablets Containing Risedronate and EDTA

Time dependent delivery tablets containing risedronate and EDTA are made by preparing a coating composition and compressed tablets containing risedronate and EDTA, and then applying said coating composition to said tablets.

A coating composition is prepared containing the following excipients, per tablet:

A. Coating Suspension

| Excipients: | |
|---|---|
| Carnauba Wax | 80 mg |
| Beeswax | 35 mg |
| Polyoxyethylene sorbitan monooleate | 11 mg |
| Hydroxypropylmethylcellulose | 24 mg |
| Purified Water | 500 mL |

The coating is prepared using the following method:

The carnauba wax, beeswax, polyoxyethlyene sorbitan monooleate, and hydroxypropylmethylcellulose are added to the purified water at 60° C. and mixed for 3 hours. The resulting coating mixture is screened and mixed throughout the coating process. The core tablets are transferred to the coating pan and preheated with occasional jogging. Tablets are coated, using a typical pan coating process until the required quantity of coating solution (at 60° C.) has been applied. Tablets are then cooled and collected in suitable containers.

A coating weight gain of 30% (total solids) is applied by spraying the above composition onto compressed tablets containing risedronate and EDTA, prepared in Part B below.

B. Compressed Tablets Containing Risedronate and EDTA

The coating suspension prepared in Part A above is sprayed onto 35 mg risedronate tablets, each tablet weighing 500 mg and each containing:

| Active Ingredients: | |
| --- | --- |
| Risedronate Sodium | 35 mg* |
| Chelant: | |
| Disodium EDTA | 150 mg |
| Excipients: | |
| Microcrystalline cellulose | 50 mg |
| Spray Dried Lactose | 245 mg |
| Sodium starch glycolate | 15 mg |
| Magnesium stearate | 5 mg |

*This amount is calculated on a risedronate anhydrous monosodium salt basis.

Tablets having the composition set forth above are prepared as follows:

The risedronate sodium, EDTA disodium, microcrystalline cellulose, Spray dried lactose and sodium starch glycolate are passed through a mill and added to a blender equipped with an intensifier bar. The mixture is blended for approximately ten minutes with the intensifier bar on. The magnesium stearate is screened and added to the blender. The blend is mixed for approximately 3 minutes with the intensifier bar off. The blend is compressed into tablets using a suitable tablet press.

Example VIII

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
| --- | --- |
| Eudragit L 30 D-55 ® (wet basis) (manufactured by Röhm Pharma GmbH and Co. KG, Darmstadt, Germany) | 47.8 mg |
| Triethylcitrate | 2.15 mg |
| Talc | 7.17 mg |
| Red Iron Oxide | 0.07 mg |
| Simethicone emulsion (30%) | 0.14 mg |
| Polysorbate 80 | 0.14 mg |
| Purified Water | 102.6 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L30 D-55® solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

The enteric coating suspension prepared in Part A above is sprayed onto 35 mg risedronate tablets, each tablet weighing 240 mg and prepared as in Example IB Example IX Enteric-Coated Soft Gelatin Capsules Containing Risedronate and Disodium EDTA Enteric-coated capsules containing risedronate and EDTA are made by preparing a coating composition and soft gelatin capsules containing risedronate and EDTA, and then applying said coating composition to said soft gelatin capsules.

An enteric coating composition is prepared in the form of a lacquer containing the following excipients, per tablet:

A. Enteric Coating Suspension

| Excipients: | |
| --- | --- |
| Eudragit L 30 D-55 ® (wet basis) (manufactured by Röhm Pharma GmbHand Co. KG, Darmstadt, Germany) | 200.0 mg |
| Dibutyl phthalate | 10.0 mg |
| Talc | 30.0 mg |
| Red Iron Oxide | 0.25 mg |
| Simethicone emulsion (30%) | 0.50 mg |
| Polysorbate 80 | 0.50 mg |
| Purified Water | 350 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and dibutylphthalate are combined and mixed for at least 45 minutes. The pigment suspension is then added to the Eudragit solution and mixed for 30 to 60 minutes. The resulting coating suspension is screened and mixed throughout the coating process. The soft gelatin capsules are transferred to the coating pan and preheated with occasional jogging. The soft gelatin capsules are coated, using a typical pan coating process until the required quantity of coating solution has been applied. Capsules are then cooled and collected in suitable containers.

A coating weight gain of 13% (total solids) is applied by spraying the above composition onto soft gelatin capsules containing risedronate and EDTA, prepared in Part B below.

B. Soft Gelating Capsules Containing Risedronate and EDTA

The enteric coating suspension prepared in Part A above is sprayed onto 50 mg risedronate soft gelatin capsules, each weighing 764 mg and each containing:

| Fill Composition | |
|---|---|
| Risedronate sodium | 50 mg* |
| Oleoyl Macrogol-6 Glycerides | 370 mg |
| Colloidal Silicon Dioxide | 5 mg |
| Disodium EDTA | 125 mg |
| Total | 550 mg |
| Gel Shell Composition | |
| Gelatin | 123.4 mg |
| Glycerin | 44.1 mg |
| Anhydrized Liquid Sorbitol (Sorbitol Special, 76%) | 27.1 mg |
| Purified Water | 17.1 mg |
| Titanium dioxide | 1.0 mg |
| FD&C Red No. 40, E129 | 0.96 mg |
| FD&C Blue No. 1, E133 | 0.30 mg |
| Total | 214 mg |
| Total Capsule weight | 764 mg |

*This amount is calculated on a risedronate anhydrous monosodium salt basis.

Soft gelatin capsules having the composition set forth above are prepared as follows:

The Oleoyl Macrogol-6 Glycerides is added to a suspension tank equipped with an overhead mixer. The risedronate sodium, disodium EDTA, colloidal silicon dioxide are passed through a mill and added to the Oleoyl Macrogol-6 Glycerides with continued mixing. The mixture is blended for approximately 60 minutes. The blend is then deaerated and ready for filling into capsules. With mixing, the glycerin, sorbitol special, and purified water are combined in a heated vacuum vessel. Heat is applied until the temperature reaches at least 80° C., then the gelatin is added and mixed for 75 minutes. The gel mass is examined for complete dissolution of particles. If needed, continued heating and mixing is applied until there is no visual evidence of undissolved particles. The gel mass is deaerated, then the titanium dioxide, FD&C Red No. 40 and FD&C Blue No. 1 are added with continued mixing. The gel mass is discharged into heated gel holding tanks for subsequent processing. The fill material is then encapsulated on a soft gelatin capsule filler.

Example X

A 65 kg woman diagnosed with postmenopausal osteoporosis is prescribed the enteric-coated oral dosage form of Example I, to be taken once weekly, comprising 35 mg risedronate and 100 mg Disodium EDTA. The patient takes the oral dosage form with breakfast once per week. The amount of risedronate absorbed is equivalent to that of a 35 mg immediate released tablet taken in a fasted state.

Example XI

A 70 kg man diagnosed with prostate cancer and high bone turnover is prescribed the enteric-coated oral dosage form of Example I, to be taken once weekly, comprising 35 mg risedronate and 150 mg citric acid. The patient takes the oral dosage form once per week, immediately before going to sleep. The patient does not experience upper GI irritation or discomfort.

Example XII

A group of women diagnosed with postmenopausal osteoporosis are prescribed the enteric-coated oral dosage form of Example IV comprising 50 mg risedronate, to be taken once weekly. The patients take the oral dosage form with breakfast once per week. The amount of risedronate absorbed is equivalent to that of a 35 mg immediate released tablet taken per label, at 30 minutes before food or drink.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral dosage form having pharmaceutically effective absorption comprising:
   (a) from about about 1 mg to about 250 mg of a bisphosphonate selected from the group consisting of risedronate and acids, salts, and esters thereof;
   (b) from about 10 mg to about 500 mg of EDTA; and
   (c) a delayed release mechanism to immediately release the risedronate and the EDTA in the small intestine; wherein said composition weighs no greater than 1 gram.

2. The oral dosage form of claim 1 wherein the EDTA is disodium EDTA.

3. The oral dosage form of claim 1 wherein the delayed release mechanism is selected from the group consisting of pH triggered delivery systems, time dependent delivery systems and mixtures thereof.

4. The oral dosage form of claim 3 wherein the delayed release mechanism is a pH triggered delivery system.

5. The oral dosage form of claim 4 wherein the pH triggered delivery system comprises an enteric coating.

6. The oral dosage form of claim 5 wherein the enteric coating disintegrates between about pH 5.5 and about pH 6.5.

7. The oral dosage of claim 5 which comprises from about 75 mg to about 250 mg of EDTA, wherein the EDTA is disodium EDTA.

8. An oral dosage form having pharmaceutically effective absorption comprising:
   (a) from about 1 mg to about 250 mg risedronate sodium;
   (b) from about 25 mg to about 500 mg of disodium EDTA; and
   (c) an enteric coating which provides for immediate release of the risedronate sodium and the disodium EDTA in the small intestine of a mammal.

9. The oral dosage form of claim 8 comprising from about 35 mg to about 50 mg of the risedronate sodium.

10. A method for treating a disease selected from the group consisting of osteoporosis, Paget's disease, hyperparathyroidism, hypercalcemia of malignancy, osteolytic bone metastasis, and combinations thereof, comprising administering to a human or other mammal in need thereof a safe and effective amount of the oral dosage form of claim 1.

11. The method of claim 10 wherein the disease is osteoporosis.

12. The method of claim 11 wherein the oral dosage form is administered according to a continuous schedule having a dosing interval selected from the group consisting of daily, weekly, three times per month, twice monthly, and once monthly.

13. The method of claim 12 wherein the oral dosage form is administered weekly.

14. The method of claim 10 wherein the oral dosage form is administered with or without food.

15. The oral dosage form of claim 8 comprising from about 15 mg to about 55 mg of the risedronate sodium.

16. The oral dosage form of claim 15 comprising from about 75 mg to about 250 mg of the disodium EDTA.

17. The oral dosage form of claim 16 comprising about 35 mg of the risedronate sodium.

18. The oral dosage form of claim 17 wherein the enteric coating is a methacrylic acid copolymer.

19. The oral dosage form of claim 17 comprising about 100 mg of the disodium EDTA.

20. The oral dosage form of claim 19 wherein the enteric coating is a methacrylic acid copolymer.

21. The oral dosage form of claim 8 comprising from about 50 mg to about 280 mg of the risedronate sodium.

22. The oral dosage form of claim 21 comprising from about 75 mg to about 250 mg of the disodium EDTA.

23. The oral dosage form of claim 22 comprising about 150 mg of the risedronate sodium.

24. The oral dosage form of claim 23 wherein the enteric coating is a methacrylic acid copolymer.

25. The oral dosage form of claim 23 comprising about 100 mg of the disodium EDTA.

26. The oral dosage form of claim 25 wherein the enteric coating is a methacrylic acid copolymer.

27. A method for treating osteoporosis comprising administering to a human or other mammal in need thereof a safe and effective amount of the oral dosage form of claim 17.

28. The method of claim 27 wherein the oral dosage form is administered with or without food.

29. A method for treating osteoporosis comprising administering to a human or other mammal in need thereof a safe and effective amount of the oral dosage form of claim 25.

30. The method of claim 29 wherein the oral dosage form is administered with or without food.

* * * * *

UNITED STATES PATENT AND TRADEMARK OFFICE
CERTIFICATE OF CORRECTION

PATENT NO. : 7,645,460 B2  Page 1 of 1
APPLICATION NO. : 11/286875
DATED : January 12, 2010
INVENTOR(S) : Dansereau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,645,460 B2 | Page 1 of 3 |
| APPLICATION NO. | : 11/286875 | |
| DATED | : January 12, 2010 | |
| INVENTOR(S) | : Richard John Dansereau et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

ON THE TITLE PAGE [56] REFERENCES CITED:

Other Publications, "Deliver" should read --Delivery--.

COLUMN 2:

Line 52, "it was" should read --it is--.

COLUMN 3:

Line 6, "instruct" should read --instructs--;
Line 8, "are" should be deleted; and
Line 9, "instructed" should read --instructs them--.

COLUMN 4:

Line 18, "is" should read --being--; and
Line 27, "active" should read --active ingredient--.

COLUMN 5:

Line 14, "active" should read --active ingredient--.

Signed and Sealed this
Eighteenth Day of January, 2011

David J. Kappos
*Director of the United States Patent and Trademark Office*

COLUMN 8:

Line 59, "active" should read --active ingredient--.

COLUMN 9:

Line 21, "the.ileum" should read --the ileum.--.

COLUMN 10:

Line 23, "acteyltriethyl" should read --acetyltriethyl--; and
Line 48, "CO.," should read --Co.,--.

COLUMN 12:

Line 52, "active" should read --active ingredient--.

COLUMN 14:

Line 4, "Eudragit L30 D-55" should read --Eudragit L30 D-55®--; and
Line 7, "Eudragit" should read --Eudragit®--.

COLUMN 15:

Line 53, "Eudragit L30 D-55" should read --Eudragit L30 D-55®--; and
Line 56, "Eudragit" should read --Eudragit®--.

COLUMN 17:

Line 2, "Eudragit L30 D-55" should read --Eudragit L30 D-55®--; and
Line 4, "Eudragit" should read --Eudragit®--.

COLUMN 18:

Line 26, "Eudragit" should read --Eudragit®--.

COLUMN 19:

Line 24, "Dibuty Sebacate" should read --Dibutyl Sebacate--;
Line 26, "Alcoholc" should read --Alcohol--;
Line 34, "dibuty sebacate" should read --dibutyl sebacate--;
Line 42, "Röhm Pharma GmbHand Co." should read --Röhm Pharma GmbH and Co.--;
Line 52, "oxide," should read --oxide--;
Line 53, "Eudragit L30 D-55" should read --Eudragit L30 D-55®--;
Line 55, "Eudragit" should read --Eudragit®--; and Line 67, "13% Enteric" should read --13% for the Enteric--.

COLUMN 21:

Line 33, "Spray" should read --spray--.

COLUMN 22:

Line 10, "Eudragit" should read --Eudragit®--;
Line 38, "Röhm Pharma GmbHand Co. KG," should read --Röhm Pharma GmbH and Co. KG,--;
Line 54, "Eudragit L30 D-55" should read --Eudragit L30 D-55®--; and
Line 57, "Eudragit" should read --Eudragit®--.

COLUMN 24:

Line 25, "about about" should read --about--.